US012765758B2

(12) United States Patent
Bin Mohamad

(10) Patent No.: US 12,765,758 B2
(45) Date of Patent: Oct. 20, 2026

(54) REINFORCED WORKING CHANNEL TUBE

(71) Applicant: AMBU A/S, Ballerup (DK)

(72) Inventor: Faiz Bin Mohamad, Penang (MY)

(73) Assignee: AMBU A/S, Ballerup (DK)

(*) Notice: Subject to any disclaimer, the term of this patent is extended or adjusted under 35 U.S.C. 154(b) by 103 days.

(21) Appl. No.: 18/817,144

(22) Filed: Aug. 27, 2024

(65) Prior Publication Data

US 2025/0072736 A1 Mar. 6, 2025

(30) Foreign Application Priority Data

Aug. 28, 2023 (EP) .................................... 23193715

(51) Int. Cl.

*A61B 1/00* (2006.01)
*A61B 1/018* (2006.01)
*A61M 25/00* (2006.01)

(52) U.S. Cl.

CPC ............ *A61B 1/018* (2013.01); *A61B 1/0011* (2013.01); *A61B 1/00009* (2013.01); *A61M 25/0012* (2013.01); *A61M 25/005* (2013.01)

(58) Field of Classification Search

CPC ... A61B 1/018; A61B 1/0011; A61B 1/00009; A61B 1/012; A61B 1/00071; A61M 25/0012; A61M 25/005; B21F 7/00; B21F 3/04; B21F 1/004

See application file for complete search history.

(56) References Cited

U.S. PATENT DOCUMENTS

| | | | | |
|---|---|---|---|---|
| 4,676,229 A * | 6/1987 | Krasnicki | .............. | A61B 1/042 600/153 |
| 4,714,075 A | 12/1987 | Krauter et al. | | |
| 6,206,824 B1 | 3/2001 | Ohara et al. | | |

(Continued)

FOREIGN PATENT DOCUMENTS

| | | |
|---|---|---|
| CN | 108599030 A | 9/2018 |
| DE | 19912199 A1 | 9/1999 |

(Continued)

OTHER PUBLICATIONS

Extended search report in European Application No. 23193715.2, dated Jan. 31, 2024, 8 pages.

*Primary Examiner* — Timothy J Neal

(74) *Attorney, Agent, or Firm* — Faegre Drinker Biddle & Reath LLP

(57) ABSTRACT

A working channel tube and a method for producing the working channel tube, the method including providing a tube reinforced with a wire coiled and embedded between an inner and outer surface of the tube, a non-embedded wire portion of the wire extending from an exit point; bending the non-embedded wire portion at a rotation location forming a bend, a first non-embedded wire sub portion and a second non-embedded wire sub portion; extending the second non-embedded wire sub portion back across the tube to a clamping location; clamping the second non-embedded wire sub portion at the clamping location in a clamp; and rotating the non-embedded wire sub portions at the rotation location such that the first and second non-embedded wire sub portions twist around each other until the wire breaks. Moreover, a working channel tube produced by said method, and an endoscope comprising said working channel tube are disclosed.

19 Claims, 6 Drawing Sheets

(56) References Cited

U.S. PATENT DOCUMENTS

| | | | |
|---|---|---|---|
| 6,315,715 | B1 | 11/2001 | Taylor et al. |
| 2007/0282304 | A1 | 12/2007 | Ogura et al. |
| 2022/0022731 | A1 | 1/2022 | Takao |
| 2022/0388055 | A1 | 12/2022 | Zou et al. |
| 2023/0110187 | A1 | 4/2023 | Matthison-Hansen et al. |

FOREIGN PATENT DOCUMENTS

| | | | |
|---|---|---|---|
| JP | 05-184533 | A | 7/1993 |
| JP | 08-122656 | A | 5/1996 |
| JP | 4859539 | B2 | 1/2012 |
| JP | 5189802 | B2 | 4/2013 |

* cited by examiner

REINFORCED WORKING CHANNEL TUBE

CROSS-REFERENCE TO RELATED APPLICATIONS

This application claims priority from and the benefit of European Patent Application No. 23193715.2, filed Aug. 28, 2023; the disclosure of said application is incorporated by reference herein in its entirety.

TECHNICAL FIELD

The present disclosure relates to a method for providing a reinforced working channel tube for an endoscope, a working channel tube made by the method, an endoscope comprising the reinforced working channel tube, and a visualization system comprising the endoscope.

BACKGROUND

Endoscopes are known and used for visual navigation into, and examination and diagnosis of, hollow organs and body cavities, as well as, optionally, to assist in surgery, e.g. for a targeted tissue sampling. Endoscopes include procedure-specialized endoscopes, such as gastroscopes and colonoscopes. Endoscopes may comprise a handle at the proximal end to be gripped by an operator and a flexible, elongated insertion cord extending distally from the handle. Alternatively, the endoscope may comprise an interface at the proximal end for cooperation with drive means, e.g. for implementation of robotic endoscopy. The insertion cord may include an insertion tube terminated in a distal tip part at the end of a highly bendable, e.g. articulated, bending section controllable by the operator. The tip part may comprise an observation optical system extending distally from the bending section.

The controllable bending section may be an articulated section at the distal tip of the elongated insertion cord. The bending section may be controlled by the operator via a control wheel arranged on the handle. The control wheel may be connected to the bending section by a steering cable. Pulling a steering cable may bend the bending section in one direction. A number of steering cables may be provided to bend the bending section to direct the distal tip in a desired direction, such as in two opposite directions or in four directions, e.g. two opposite directions in a first plane and two opposite directions in a second plane at right angles to the first plane.

Thus, using the control wheels allows the operator to advance the distal tip of the endoscope to a desired location by means of a series of actions involving, inter alia, bending the bending section in a desired direction, advancing the elongated insertion cord, and twisting the elongated insertion cord.

Endoscopes usually comprise an internal working channel extending from the working channel access port of the endoscope handle to the distal tip unit of the insertion cord, providing a multi-function channel from the handle to the distal tip. The working channel may be used for guiding a surgical tool through the internal working channel into the patient's body cavity, i.e. distally with respect to the tip of the endoscope. Additionally, the internal working channel may typically also be used as a suction channel to aspirate for example body fluid from an operation area within the patient's body cavity and/or as an irrigation channel for supplying fluid to the operation area or to an area from which a sample is to be collected through aspirating and collecting the supplied fluid as is for example done in a bronchoalveolar lavage procedure.

Internal working channels are usually formed by a connector part, the so-called biopsy connector or Y-connector, a flexible working channel tube arranged inside the endoscope handle, the insertion tube and the bending section, and a tip housing of the distal tip unit.

In addition to internal working channels there are also already known external working channels which can be mounted to the insertion cord of an endoscope from outside and which may serve as an additional lumen for guiding instruments into the patient's body cavity, for aspirating body fluids from the operation area, etc.

Both internal and external working channels usually comprise a flexible working channel tube having an elongated hollow tube main body usually made of a polymer material.

When the actively bendable bending section of the insertion cord is bent, e.g. by manually operating a wheel or lever provided at the endoscope handle, there is the danger that a kinking of the working channel tube occurs due to insufficient stability. Kinking usually goes along with a change of the shape of the cross section of the working channel tube. In particular, the cross-sectional shape of the working channel tube is in sections not circular anymore. This may affect a movement of instruments inside the working channel tube and a suction performance especially if the kinking causes a constriction of the working channel tube.

Therefore, it is desirable to reduce or avoid the risk of kinking of the working channel tube during operation of the endoscope, in particular during bending of the actively bendable bending section. It is in this light previously suggested to provide reinforced working channel tubes.

Known reinforced working channel tubes have the problem that they are costly because they are made by manufacturing methods that involve high cost and complexity. Additionally, existing reinforcing methods may not be suitable to reinforce very small working channel tubes with very small wall thicknesses without increasing the outer diameter of working channel tube which goes against the general desire within the field of endoscopy to provide an endoscope where the insertable part has as small an outer diameter as possible to reduce the invasiveness of a surgical procedure in which the endoscope is used. Adding to this, some of the reinforcing materials used, e.g. knitted or braided fabrics, may unacceptably reduce the flexibility of the bending section, particularly when used in very small working channel tubes with very small wall thicknesses.

SUMMARY

It is an object of the present disclosure to provide a solution which at least improves on the solutions of the prior art. Particularly, it is an objective of the present disclosure to provide a method for producing a reinforced working channel tube with minimal change of inner and outer dimensions of the working channel tube. Further to provide a method enabling reinforcing a longitudinal section of the working channel tube to tailor the properties of the tube.

In a first aspect, a method for producing a wire coil reinforced working channel tube is provided.

In an embodiment according to the first aspect, the method comprises: (a) providing a working channel tube reinforced with a wire coil that is embedded between an inner and an outer surface of the working channel tube, wherein a non-embedded wire portion of the wire coil extends out of the outer surface of the tube from an exit point, wherein an exit point tangent line that is tangent to the outer surface at the exit point defines two opposite directions extending away from the exit point: (i) an unembedded direction extending away from a final embedded wire portion leading up to the exit point; and (ii) an embedded direction that is opposite the unembedded direction, wherein an exit plane extends through the exit point and a longitudinal axis of the tube, the space extending in the unembedded and embedded directions from the exit plane being defined as the unembedded space and an embedded space, respectively; (b) fixating the working channel tube; (c) extending the non-embedded wire portion from the exit point to a rotation location located in the unembedded space; (d) bending the non-embedded wire portion at the rotation location forming a bend and a first non-embedded wire sub portion extending from the exit point to the bend and a second non-embedded wire sub portion extending after the bend; (e) extending the second non-embedded wire sub portion back across the tube to a clamping location located in the embedded space; (f) clamping the second non-embedded wire sub portion at the clamping location in a clamp; and (g) rotating the non-embedded wire sub portions at the rotating location such that the first and second non-embedded wire sub portions twist around each other until the wire breaks.

An advantage of this method is that it provides a reinforced working channel tube with minimal wire protrusion in a simple, efficient, repeatable, and low-cost manner. It further facilitates the breaking of the wire coil wire beneath the outer surface of the tube meaning there is no wire protrusion from the outer surface of the tube. This can also eliminate the need for potential postprocessing to reduce the impact of any wire protrusion e.g. by cutting, grinding, or covering an existing protrusion with an adhesive or another material, which are often labor-intensive processes. As alluded to in the background section, providing an assembled endoscope with such a tube can improve the mobility thereof whilst having the kink resistance of a reinforced working channel tube.

The wire coil reinforced working channel tube may be provided in a variety of ways as is known to the person skilled in the art. One example may include providing a working channel tube made from a plastic material, softening the outer surface of the tube by heat and winding a wire into the outer surface of the tube thereby forming a wire coil embedded in the tube. The wire may be helically wound into the outer surface. Softening the outer surface of the tube may involve melting the surface. A reinforced working channel tube and a method for its production are disclosed in commonly-owned U.S. Patent Publication No. 2023/0110187, published Apr. 23, 2023, which is incorporated herein in its entirety. As described therein, the method comprises providing a tube main body having a longitudinal axis, the tube main body being an elongate hollow tube having an outer surface comprising a meltable plastic material; providing a wire; heating a portion of the wire; winding the heated portion of the wire under tension around the outer surface of at least a portion of the tube main body to form a coil having a coil pitch, the heated portion of the wire softening or melting the outer surface and penetrating through the softened or melted outer surface of the tube main body; and allowing the softened or melted outer surface of the tube main body to cool, wherein after cooling the coil is affixed to the tube main body. According to the method according to the first aspect, after said cooling and while the tube main body is secured (as while the polymer is softened or released and resecured later), the wire is twisted under tension to cause it to break at the exit point from the polymer into which it is embedded or inside the polymer so that the broken end does not protrude from the polymer. Said securement and twisting are as described in the present disclosure, which cause the breakage to occur as desired.

In a variation of the present embodiment, the outer surface may be softened and/or melted using chemicals. The solidifying of the plastic material of the tube may act to anchor the wire coil in the tube.

The working channel tube being fixated helps to ensure that tube does not move when rotating the first and second non-embedded wire sub portions at the rotation location which creates a pulling force on the tube through the first non-embedded wire sub portion thus allowing tension to build up in the wires.

In a variation of the present embodiment, the working channel tube is fixated such that translational as well as rotational movement is prevented. For example, the working channel tube may be fixated by clamping it in place and/or by pressing into press fit retainers. The press fit retainers may for example be U-shaped, V-shaped, trough shaped, etc. The working channel tube may be fixated at more than one fixation location such as 2, 3, 4, 5, 6, 7 or more. The working channel tube may at least be fixated at a location proximal of and at a location distal of a respective exit point. Proximal may be understood as a direction towards the handle of an assembled endoscope and distal may be understood as a direction towards the distal tip of an assembled endoscope. It may be fixated such that there is a fixation location within 10 working channel tube outer diameters or less proximally of a respective exit point and a fixation location within 10 working channel tube outer diameters or less distally of the respective exit point. This may facilitate the method by ensuring the tube is supported and fixated optimally to prevent moving and bending of the tube during the rotation of the wires which may negatively impact the outcome of the method.

The rotation location being located in the unembedded space helps to prevent that the pull on the embedded wire from a first non-embedded wire sub portion created by the rotating and twisting of the wire sub portions is in a direction that pulls out the embedded wire.

Rotating at the rotation location may be substantially about a longitudinal axis of the first non-embedded wire sub portion extending between the exit point and the rotation location. The rotating of the non-embedded wire sub portions such that they twist around each other creates a tension in the wires and further may act to fatigue the wires, causing the wire to break, in a simple and controllable manner. The wire may break due to a torsional break which may be beneath or flush with the outer surface of the tube.

In another variation of the present embodiment, the rotation location may comprise a clamp which clamps in place the first and second sub wire portions. If such a clamp is provided, in step (g), the clamp may be rotated to rotate the wires at the rotation location until the wire(s) break. Alternatively to such a clamp, the rotation location may comprise a geometry, such as for example a hook or ring, around which the non-embedded wire portion may be bent in step (d) such that the bend is formed around the geometry, wherein in step (g) the geometry may be rotated to rotate the non-embedded wire sub portions at the rotation location until the wire breaks. A rotator, for example an electric motor, may be used to provide the rotation.

Bending the non-embedded wire portion at the rotation location and extending the second non-embedded wire sub portion back across the tube to a clamping location located in the embedded space helps to ensure that the first and second non-embedded wire sub portions will twist around each other and form windings from the rotation location to the exit point when rotating the non-embedded wire portions at the rotation location. The forming of windings of the non-embedded wire sub portions from the rotation location to the exit point helps to ensure a clean break of the wire below the outer surface of the tube. Extending the second non-embedded wire sub portion back across the tube may be understood as extending the second non-embedded sub portion back over the portion of the tube where the exit point is located. The second non-embedded wire sub portion may be extended back across the tube through a space normal to the exit point. The second non-embedded wire sub portion may be extended back across the tube such that at least a section of the second non-embedded wire sub portion extends over the exit point normal to the exit point and tube outer surface. The second non-embedded wire sub portion may extend back across the tube in a substantially straight line. In a variation of the present embodiment, the second non-embedded wire sub portion extends back across the tube substantially parallel to the first non-embedded wire sub portion.

In another variation of the present embodiment, the second non-embedded wire sub portion is clamped and is configured to allow slippage of the wire such that a length of the wire slides out of the clamp when pulled. Slippage helps to ensure that windings of the first and second non-embedded wire sub portions around each other can keep forming from the rotation location up to the exit point. It is to be understood that clamping the second non-embedded wire sub portion such that it can slip means that as the two non-embedded wire sub portions rotate and twist around each other and create tension in the wire sub portions, the second non-embedded wire sub portion is pulled through the clamp at the clamping location by the tension. In other words, it is clamped such that allowing the second non-embedded wire sub portion to be pulled through the clamp when the sub wire portion is pulled. This has been found to facilitate that it is the wire beneath the tube outer surface at the exit point that breaks when rotating the wires and not the second non-embedded wire sub portion. At present it is believed that a reason for this may be that the tension will be higher in the first non-embedded wire sub portion than in the second non-embedded wire sub portion. The term “such that it can slip” may alternatively be termed “such that it is held loosely” i.e. allowing the second non-embedded wire sub portion to be pulled through the clamp when the second non-embedded sub wire portion is pulled.

In an alternative variation of the present embodiment, the second non-embedded wire sub portion is clamped at the clamping location in a clamp that fixates the second non-embedded wire sub portion in the clamp. This may be understood as a clamp that does not allow slippage of wire and/or prevents slippage of the wire.

In a further variation of the present embodiment, the rotation location is located in the unembedded space such that a rotation angle in a direction normal to the exit point and the tube outer surface between a straight line extending from the exit point to the rotation location and the exit point tangent line is 45 degrees or less.

This may result in a cleaner break of the wire as the angle at which tensile forces and the torsional forces from rotating and twisting of the non-embedded wire sub portions act on the embedded wire is reduced. Further, it may prevent any embedded wire from being pulled out of the tube as tension builds up in the wires during the production. Alternatively, the rotation angle in a direction normal to the exit point and the tube outer surface between a straight line extending from the exit point to the rotation location and the exit point tangent line may be 40, 35, 30, 25, 20, 15, 10, 9, 8, 7, 6, 5, 4, 3, 2, or 1 degree(s) or less. In another variation of the present embodiment, the rotation location may be located on the exit point tangent line. In general, the rotation angle between the exit point tangent line and a straight line extending from the exit point to the rotation location may be 45, 40, 35, 30, 25, 20, 15, 10, 9, 8, 7, 6, 5, 4, 3, 2, or 1 degree(s) or less. Similarly, in a variation of the present embodiment the rotation angle and/or the clamping angle between a straight line extending to the rotation location or clamping location respectively and a lateral plane extending through the exit point perpendicularly to the exit plane may be 45, 40, 35, 30, 25, 20, 15, 10, 9, 8, 7, 6, 5, 4, 3, 2, or 1 degree(s) or less. This can improve yield and reduce variance of the produced tubes. Alternatively, the rotation angle may be the angle measured between the exit point tangent line and the first non-embedded wire sub portion extending to the rotation location from the exit point, potentially just before rotating the non-embedded wire sub portions. The rotation location may be the point at which the first and/or second non-embedded wire sub portion(s) is/are rotated. Alternatively, the rotation angle may be measured between the exit point tangent line and a straight line extending from the exit point to the apex of the bend of the non-embedded wire portion after forming the bend at the rotation location.

In another variation of the present embodiment, the clamping location is located in the embedded space such that a clamping angle between the exit point tangent line and a straight line extending from the exit point to the clamping location is 45 degrees or less.

In another variation of the present embodiment, the rotation angle and the clamping angle is equal to or less than 10 degrees.

In another variation of the present embodiment, the rotation location and the clamping location are located beyond the working channel tube.

This may be understood as the rotation and clamping location being located such that there is a spacing between the tube and rotation and clamping locations. This can improve the ease with which the method can be performed as there are less spatial restrictions on the rotation location and clamping location when located beyond the tube.

In an example of the present variation, there is a distance of 0.5 or more but equal to or less than 10 working channel tube outer diameters between the exit plane and the rotation location and the exit plane and the clamping location respectively, the distance being measured perpendicularly to the exit plane.

The rotation and clamping location may be located beyond the working channel tube such that there is a distance of 1, 2, 3, 4, 5, 6, 7, 8, 9, 10, 11, 12, 13, 14, 15, 16, 17, 18, 19, or 20 or more working channel tube outer diameters between the rotation location and exit plane of the working channel tube and/or clamping location and exit plane, respectively i.e. the rotation and clamping location may respectively be located with different distances to the outer surface of the tube. There may equal to or less than 100, 90, 80, 70, 60, 50, 40, 30, 20, 10, or 5 working channel tube outer diameters between the rotation location and the exit plane and/or between the clamping location and the exit plane, respectively. For example, there may be equal to or more than 1 working channel tube outer diameters, but less than 30 working channel tube outer diameters between the rotation location and the exit plane and/or between the clamping location and the exit plane, respectively. The distance between the exit plane and the clamping location and/or rotation location may be measured perpendicularly to the exit plane. The distance between the clamping location and the exit plane may be defined as the perpendicular distance between the exit plane and the portion closest to the exit plane of the clamp the second non-embedded wire sub portion is clamped in at the clamping location. The distance between the rotation location and the exit plane may be defined as the perpendicular distance between the exit plane and the point at which the first and second non-embedded wire sub portions are rotated. Alternatively, it may be defined as the perpendicular distance between the exit plane and the portion closest to the exit plane of the portion of the first and second non-embedded wire sub portions that is rotated at the rotation location. The distance between the rotation location and the exit plane may be defined as the perpendicular distance between the exit plane and the portion closest to the exit plane of the means used to rotate the first and second non-embedded wire sub portions at the rotation location such as for example a clamp, hook, or ring etc.

In another variation of the present embodiment, a second non-embedded wire portion of the wire coil extends out of the outer surface of the tube from a different second exit point defining respective unembedded and embedded directions, wherein steps (c) to (g) are performed for the second non-embedded wire portion respectively.

In this way, if a there are two non-embedded wire portions extending from the outer surface of the working channel tube, for example one at each end of the wire coil, then both wire portions can be broken in the same method to efficiently provide a reinforced working channel tube according to the present disclosure.

In another variation of the present embodiment, the working channel tube is fixated such that there is a fixation location within 10 working channel tube outer diameters or less proximally of a respective exit point and a fixation location within 10 working channel tube outer diameters or less distally of the respective exit point.

In variation of the present embodiment, a rod is inserted into the working channel tube before fixating it in place.

This may be done to prevent that the tube is damaged or collapses when clamped. The rod may further provide rigidity to the working channel tube when rotating the wires which may facilitate the wire breaking process and prevent damage to the working channel tube. The rod may be made of a rigid material e.g. a plastic or a metal. In an example of the present variation, a metal rod is inserted into the working channel tube before it is press fit into 7 U-shaped shaped press fit retainers at 7 different locations along the working channel tube.

In an example of the present variation, the rod is at least inserted a length such that it extends inside the working channel tube at each location the working channel tube is fixated and/or at each exit point.

In another example of the present variation, a mandrel is inserted instead of the rod. The mandrel may comprise movable pins or longitudinal pivotable parts (collectively, the "securing features") which can be caused to extend outwardly to secure the mandrel, in a releasable manner, to the reinforced working channel tube. Air pressure may be used to cause the securing features to move or rotate to secure the reinforced working channel tube. Alternatively, a longitudinal portion is inserted in a slot on the mandrel and, when the longitudinal portion is translated in the slot, portions of it extend outwardly from the surface of the mandrel to secure the reinforced working channel tube.

In another variation of the present embodiment, the embedded wire coil extends equal to or less than three quarters of a length of the working channel tube.

In this way a working channel tube can be provided which is reinforced in a specific portion of the tube where reinforcing may be desired. Further, this can reduce cost of the reinforced working channel tube as less wire coil needs to be used compared to reinforcing a larger length or the entire length of the tube, and, no less importantly, using less material can provide a more sustainable product. In a variation of the present embodiment, the wire coil may extend equal to or less than 7⁄10, 3⁄5, 1⁄2, 2⁄5, 3⁄10, 1⁄5 or 1⁄10 of the length of the working channel tube. In an alternative embodiment, the wire coil may extend more than three quarters of the length of the working channel tube, potentially up to and equal to the entire length of the working channel tube may be reinforced. It is to be understood that the reinforced working channel tube produced by said method may be a working channel tube which is entirely reinforced, i.e. over its entire length, or which is only reinforced in one or more sections, over only a portion of its entire length, i.e. only locally. A section may be a division of the full length of the tube, such as extending substantially only the length along a bending section of the assembled endoscope. For example, the working channel tube may for example only be reinforced along the length of the bending section when assembled in an endoscope. In other words, the wire coil may be provided only along the section of the working channel tube where the bending section is located in an assembled endoscope.

In another variation of the present embodiment, at least an outer layer of the working channel tube wall is made from a plastic material.

In another variation of the present embodiment, the wall of the working channel tube may be a single layer of material or may comprise two or more layers of material, such as for example an inner layer and an outer layer. The working channel tube may comprise an outer layer comprising the outer surface and an inner layer comprising the inner surface. The material of the outer layer may be different from the material of the inner layer. When the two layers, i.e. the outer layer and the inner layer, are made of different material, each layer may be optimized for its specific purpose. The outer layer may be made of a meltable plastic material that is configured to melt or soften when it is heated, for example to allow reinforcing of the working channel tube by allowing the hot wire of the heated reinforcing wire coil to melt or soften the outer layer and cut into the same when it is wound around the working channel tube when producing a reinforced working channel tube. The inner layer may be made of a meltable plastic material, however, does not have to be made of the same, as it is not intended to be melted or softened. The inner layer and thus its material may be optimized for other purposes, e.g. enabling a smooth gliding of an instrument inside the working channel tube. The outer layer may e.g. be made of TPU (thermoplastic polyurethane). The inner layer may be made of HDPE (high-density polyethylene). The reinforcing wire coil may be embedded in only one of the layers or in more than one of the layers or in all of the layers. The working channel tube may also an integral part made of only one meltable plastic material, thus not comprising the outer layer and inner layer made of different materials.

Optionally, a primer may be provided between the inner layer and the outer layer to ensure and increase an adherence between the two layers. This is e.g. of advantage if the outer layer is made of TPU (thermoplastic polyurethane) and the inner layer is made of HDPE (high-density polyethylene). The working channel tube may be coextruded, thus the inner, tie or primer, and outer layers are extruded simultaneously.

In another variation of the present embodiment, the outer diameter of the working channel tube may equal to or less than 15 mm, 14 mm, 13 mm, 12 mm, 11 mm, 10 mm, 9 mm, 8 mm, 7 mm, 6 mm, 5.5 mm, 5 mm, 4.5 mm, 4 mm, 3.5 mm, or 3 mm. The outer diameter of the working channel tube may for example be in the range of 1.5 mm to 10 mm. The wall thickness of the working channel tube, i.e. the radial thickness of the material between the outer surface and inner surface of the working channel tube may be equal to or less than 1.5 mm, 1.4 mm, 1.3 mm, 1.2 mm, 1.1 mm, 1 mm, 0.9 mm, 0.8 mm, 0.7 mm, 0.6 mm, or 0.5 mm. The wall thickness may for example be in the range of 0.1 mm to 0.7 mm. This may provide the optimum compromise between working channel diameter, i.e. the diameter of the hollow channel extending through the working channel tube, outer diameter of the working channel tube, bending performance and durability.

The inner layer may be thinner than the outer layer, or said differently, a wall thickness of the inner layer may be smaller than a wall thickness of the outer layer. E.g. the inner layer may have a thickness of between 0.050 mm to 0.080 mm and the outer layer may have a thickness of between 0.32 mm to 0.35 mm. However, other layer thicknesses are conceivable, and it is also conceivable that the thickness of the inner layer is greater than the thickness of the outer layer. The working channel tube wall may have a wall thickness of less than 0.5 mm, or less than 0.4 mm.

In another variation of the present embodiment, the diameter of the wire of the reinforcing wire coil may be equal to or less than 0.5 mm, 0.45 mm, 0.4 mm, 0.35 mm, 0.3 mm, 0.25 mm, 0.2 mm, 0.153 mm, 0.15 mm, 0.128 mm, 0.102 mm, 0.10 mm, 0.08 mm, or 0.05 mm. The diameter of the wire may for example be in the range of 0.01 mm to 0.25 mm or 0.05 mm to 0.15 mm. The diameter of the wire may be between 0.08 mm and 0.15 mm. In an example of the present variation, the outer diameter of the working channel tube is 5.4 mm with a wall thickness of 0.5 mm and the diameter of the wire is 0.15 mm. The diameter of the wire may alternatively be the thickness of the wire.

The working channel tube may have a wall thickness of less than 0.4 mm, and may comprise an inner layer having a thickness of between 0.050 mm to 0.080 mm, an outer layer having a thickness of between 0.32 mm to 0.35 mm, and a coil with a coil pitch between 0.5 mm and 1.5 mm, or between 0.8 mm and 1.2 mm, or about 1.0 mm. The wall thickness of the working channel tube may at least two times greater than the diameter or thickness of the wire.

In another variation of the present embodiment, the wire of the reinforcing wire coil may be a single strand wire. The wire may be made of a ductile material. The wire may be a metal wire, for example the wire may be made of SUS 304. In an example of the present variation, the wall of the working channel tube comprises two layers in the form of an inner and outer layer and the outer diameter of the working channel tube is 3.65 mm with a wall thickness of 0.39 mm, the diameter of the wire is 0.10 mm SUS 304 and it is embedded in the outer layer of the tube wall.

In another variation of the present embodiment, a reinforced working channel tube may be provided with several sections having an embedded wire coil and (b) to (g) may be repeated for each section of embedded wire coil to provide a reinforced working channel tube comprising several reinforced sections.

In a second aspect, a working channel tube is provided. The working channel tube is produced according to the method of the first aspect including variations and examples thereof.

In a third aspect, an endoscope comprising a reinforced working channel tube according to the second aspect is disclosed.

In a fourth aspect, a system comprising a video processing apparatus (VPA) and an endoscope according to the third aspect is provided, wherein the video processing apparatus (VPA) is couplable to the endoscope and capable of processing an image recorded by the endoscope and outputting the image on a display is disclosed.

In a variation of the present embodiment of the fourth aspect, the video processing apparatus may comprise a built-in display for displaying the image outputted by the VPA. The VPA may be wirelessly couplable to the endoscope or via a wired connection.

BRIEF DESCRIPTION OF THE FIGURES

The disclosure will now be made in greater detail based on non-limiting exemplary embodiments and with reference to the drawings, on which.

The figures are schematic in nature and serve only to understand the disclosure. The features of the different embodiments can be interchanged among each other.

DETAILED DESCRIPTION

Figure 1:
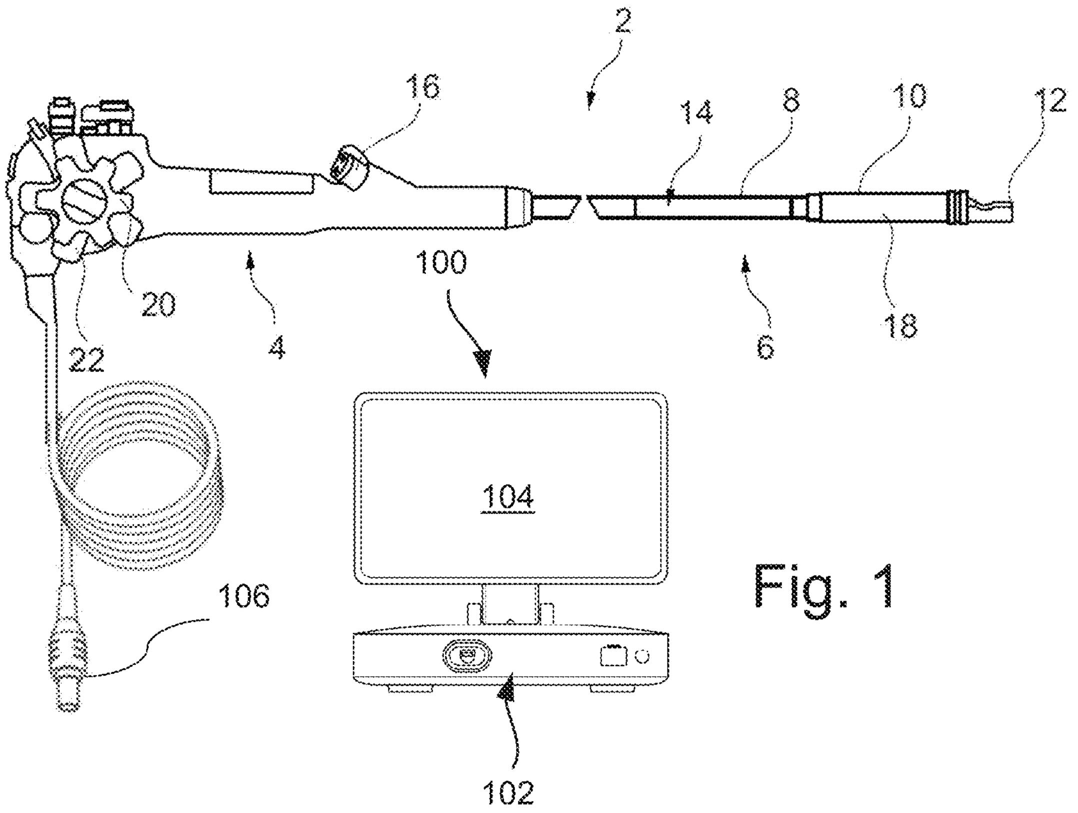
FIG. 1 shows a schematic view of a visualization system comprising an endoscope and a video processing apparatus according to the present disclosure.

FIG. 1 is a schematic side view of a visualization system 100 including an endoscope 2 with a cable connector 106, which can be connected to an endoscope connection port (not shown) of the video processing apparatus (VPA) 102. A VPA can incorporate a display screen 104 or, as shown, can be connected to a "separable" display screen. The VPA can be communicatively connected, as is known in the art, via an ethernet, wireless, AVI, HDMI, or other data interfaces to a separable display screen 104. Upon connection of the endoscope the VPA presents images or video streams with the display screen, as is known in the art. The endoscope 2 has a proximal endoscope handle 4 and an insertion cord 6 extending distally from the endoscope handle 4. The insertion cord 6 is configured to be inserted into a patient's body cavity and comprises an insertion tube 8, an actively bendable bending section 10 and a distal tip unit 12. The endoscope 2 further comprises a working channel 14 which extends from a working channel access port 16 provided at the endoscope handle 4 to the distal tip unit 12. The working channel 14 is comprised by a working channel tube 18, which is arranged inside the endoscope handle 4, the insertion tube 8 and the bending section 10. The endoscope handle 4 comprises two operating units 20, 22 formed as wheels for steering the bending section 10 of the insertion cord 6. In particular, a rotation force can be applied to both the first operating unit 20 and the second operating unit 22 by a user in order to bend the bending section 10 in two bending planes i.e. four directions. The endoscope 2 may alternatively be formed as a one-plane bending endoscope which can be bent only in two, preferably opposite, directions and which has only one operating unit 20, 22. In addition to wheels, operating units may comprise levers as are well known in the art. The endoscope may be a single-use endoscope.

Figure 2:
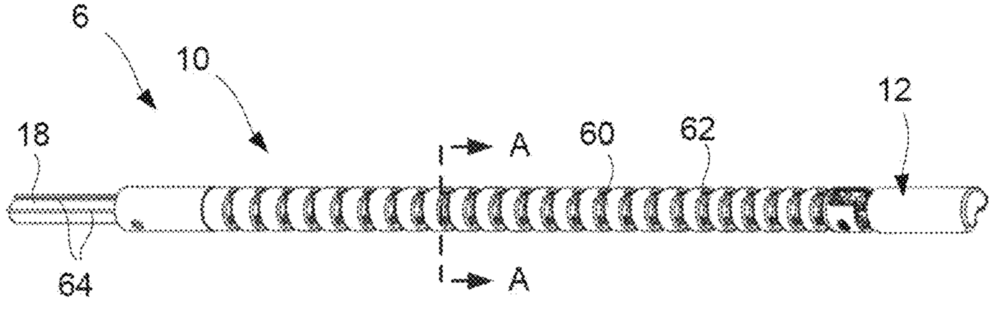
FIG. 2 is a side view of a bending section showing a working channel tube.
Figure 3:
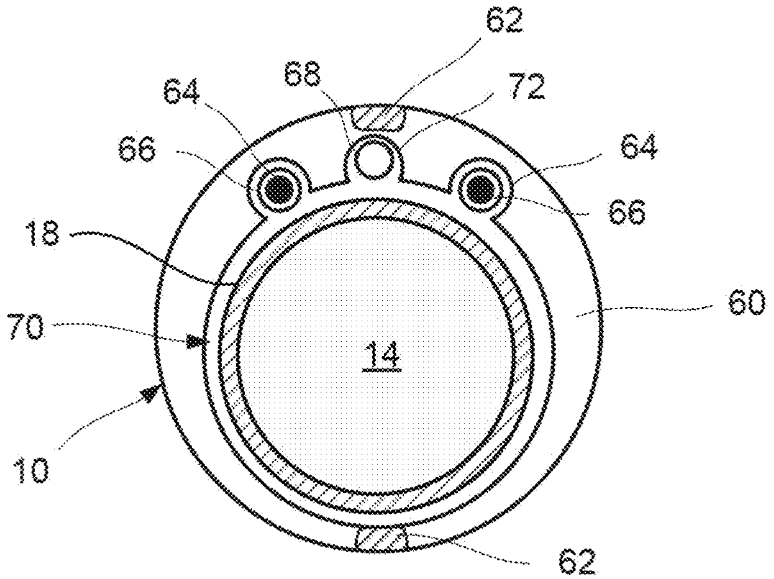
FIG. 3 is cross-section A-A of the bending section of FIG. 2.

FIG. 2 shows an embodiment of a bending section 10 showing a working channel tube 18 (the reinforcement is not shown). FIG. 3 is cross-section A-A of the bending section of FIG. 2 showing a spacing 70 in which the working channel tube 18 is positioned. The bending section 10 may comprise a single-piece polymeric structure comprising a plurality of segments 60 interconnected by polymeric strips 62, or hinges, which form part of the one-piece structure and bend upon tensioning of steering cables 64 by operation of the operating unit 20. The working channel 14 may be configured to introduce a surgical tool therethrough. In FIG. 3, a wall of the segment 60 defines the spacing 70 and a number of cut-out lobes 72 extending from the periphery of the inner surface of the segment 60 through which steering cable guide tubes 66 and the steering cables 64 pass. A sleeve (not shown) may be provided over the bending section 10 to fluidly seal the spaces between adjacent segments 60. Wires 68 pass through one of the cut-out lobes 72 and connect a camera positioned in the distal tip of the insertion cord 6 to the handle 4. A cable having a cable connector 106 connects the wires 68 to a VPA 102 shown in FIG. 1.

Space in the bending section is limited and becomes even more limited as the diameter of the insertion cord 6 is reduced to minimize the invasiveness of the surgical procedure in which the endoscope 2 is used. These reductions require smaller working channel tubes with smaller wall thicknesses, and the working channel tubes with reduced wall thickness benefit from the disclosed reinforcement. Any protrusions from the outer surface of the working channel tube, such as for example wire from a reinforcing wire coil, will reduce the gained benefit of using working channel tubes with smaller wall thicknesses as the protrusions will take up some or all of the space saved by using smaller wall thickness working channel tubes. Furthermore, such protrusions may create additional friction and resistance to bending and maneuvering the endoscope especially if they contact and catch on the inner surface of the insertion tube 8. If other fluid tubes are provided inside the insertion tube, particularly if they are made of a plastic, as may often be the case, such protrusions may catch on, damage, or even pierce these fluid tubes Therefore, any such protrusion should preferably be avoided.

The working channel tube 18 provided inside the endoscope handle 4, the insertion tube 8 and the bending section 10 is a specific reinforced working channel tube 18 according to the present disclosure and is in particular reinforced in a portion of the working channel tube 18 which is arranged inside of the bending section 10, in order to prevent kinking of the working channel tube 18 when the bending section 10 is bent. It is also possible to reinforce the entire working channel tube 18, i.e. not only the portion of the working channel tube 18 which is arranged inside the bending section 10 of the insertion cord 6, or other portions of the working channel tube 18. Further, the working channel tube 18 does not need to be arranged inside the insertion cord 6 but may, alternatively, be attached to the insertion cord 6 from outside.

Figure 4:
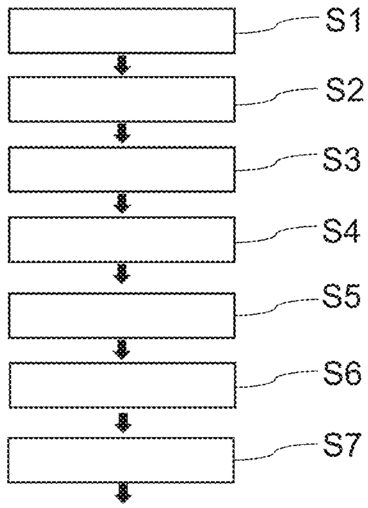
FIG. 4 shows a flow chart of a method for producing a reinforced working channel tube according to the present disclosure.

With reference to FIGS. 4-10 a method for producing a wire coil reinforced working channel tube 18 for an endoscope according to the present disclosure will be described. FIG. 4 shows a flow chart of the method for producing a reinforced working channel tube 18. In a first step S1, a working channel tube 18 reinforced with a wire coil 33 that is embedded between an inner 26 and outer 28 surface of the working channel tube is provided. A non-embedded wire portion 30 of the wire coil 33 extends out of the outer surface 28 of the tube 18 from an exit point 29 and an exit point tangent line 34 that is tangent to the outer surface 28 at the exit point 29 defines two opposite directions extending away from the exit point 29, an unembedded direction UD extending away from a final embedded wire portion 35 leading up to the exit point 29, and an embedded direction ED that is opposite the unembedded direction UD as seen e.g. in FIG. 7. Further, an exit plane 36 extends through the exit point 29 and the longitudinal axis L of the tube 18, the space extending in the unembedded and embedded directions from the exit plane being defined as the unembedded space and embedded space, respectively.

In a step S2, the working channel tube 18 is fixated. The non-embedded wire portion 30 is then extended from the exit point 29 to a rotation location 40 in the unembedded space in a step S3. In a further step S4, the non-embedded wire portion 30 is bent at the rotation location 40 forming a bend 41 and a first non-embedded wire sub portion 31 extending from the exit point 29 to the bend 41 and a second non-embedded wire sub portion 32 extending after the bend 41. In a step S5 the second non-embedded wire sub portion 32 is extended back across the working channel tube 18 to a clamping location 42 located in the embedded space. In a step S6 the second non-embedded wire sub portion 32 is clamped at the clamping location 42 in a clamp configured to allow slippage of the wire 32 such that a length of the wire slides out of the clamp when pulled. In a step 7 the non-embedded wire sub portions 31, 32 are rotated at the rotation location 40 such that the first and second non-embedded wire sub portions 31, 32 twist around each other until wire breaks (twisting of the wires is shown in e.g. FIG. 8). The order of the steps described here is merely one example within the scope of this disclosure. In other variations of the present embodiment the order may be different, for example the non-embedded wire portion 30 may be bent before it is extended to the rotation location 40, the second non-embedded wire sub portion 32 may be extended across the tube 18 to the clamping location 42 and potentially clamped there before the non-embedded wire portion 30 is extended to the rotation location 40, the working channel tube 18 may be fixated after the non-embedded wire portion 30 has been bent at the rotation location 40 and/or after the second non-embedded wire sub portion 32 has been clamped at the clamping location 42.

As also mentioned in the summary section the wire coil reinforced working channel tube 18 may be provided in a variety of perceivable ways as is known to the person skilled in the art. In this example it is provided by providing a working channel tube made from a plastic material, softening the outer surface 28 of the tube 18 by heat and helically winding a wire 38 into the outer surface of the tube thereby forming a wire coil 33 embedded in the tube 18 and the working channel tube.

Figure 5:
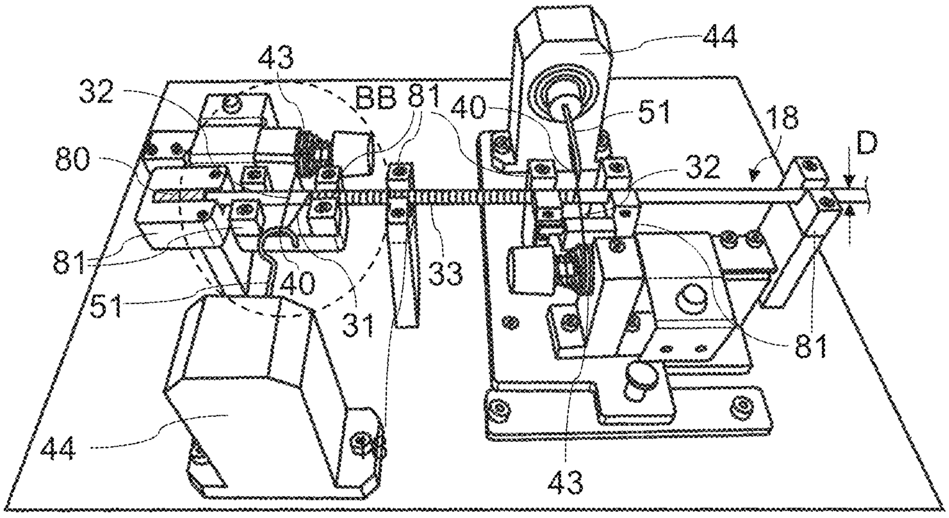
FIG. 5 shows a perspective view of a working channel tube in a wire breaking machine during production according to a method of the present disclosure.
Figure 6:
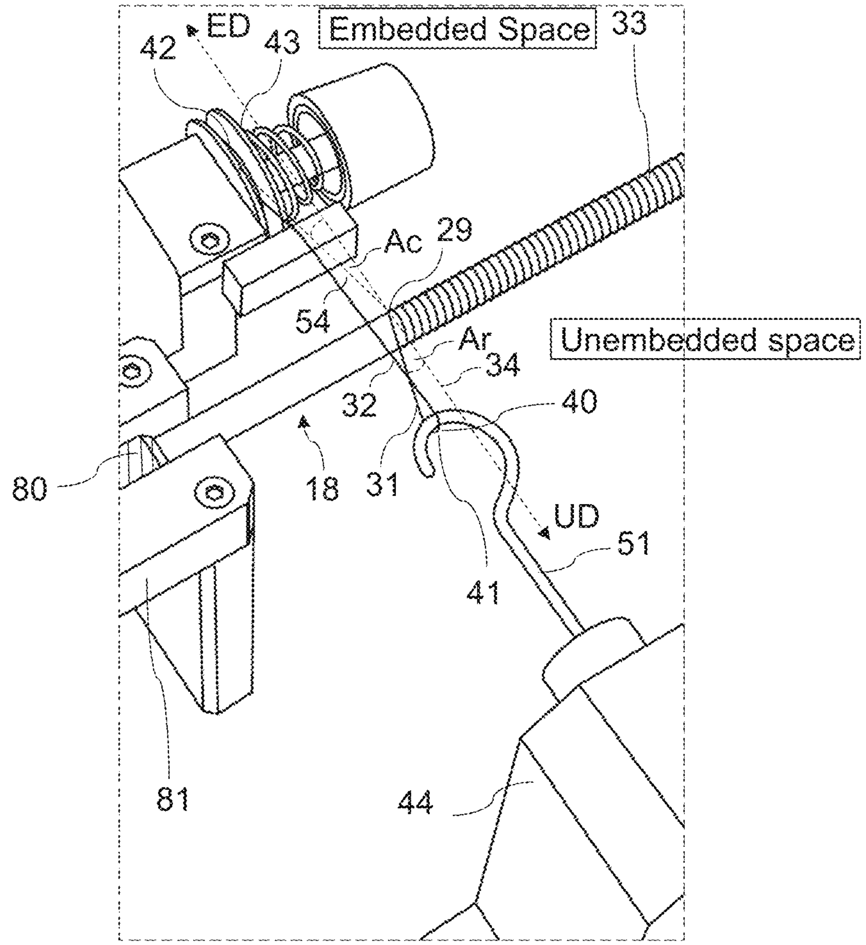
FIG. 6 shows a close-up of the detail BB in FIG. 5.

FIG. 5 and FIG. 6 show the wire coil reinforced working channel tube 18 in a wire breaking machine during production. Before fixating the tube 18 a rigid metal rod 80 has been inserted into the tube 18. The working channel tube 18 has then been fixated such that translational as well as rotational movement is prevented by press fitting it into 7 U-shaped press fit retainers 81 at 7 different fixation locations 81 along the working channel tube 18. The metal rod 80 extends inside the working channel tube 18 at each location 81 it is fixated and at each exit point 29. There is a fixation location 81 within 5 working channel tube outer diameters D proximally and distally of each respective exit point 29. The two non-embedded wire portions 30, one at each end of the wire coil 33, have respectively been extended from their respective exit point 29 to a respective rotation location 40 located in the unembedded space and comprising a hook 51 around which they have been bent to form a bend 41 and respective first and second non-embedded wire sub portions 31, 32. Instead of a hook 51, any other suitable geometry could be used, for example the rotation location could comprise a ring (not shown) through which the non-embedded wire portions 30 could be threaded and bent around forming a bend 41 similar to how the non-embedded wire is bent around the hooks 51 in FIG. 5 and FIG. 6. Alternatively instead of a hook or ring the rotation location could comprise a clamp 52 such as shown in FIG. 7 to FIG. 10 where the non-embedded wire portion 30 is bent inside the clamp 52, which then clamps the first and second non-embedded wire sub portions 31, 32 in place before being rotated through help of the attached electric motor 44.

After bending round the hooks 51, the second non-embedded wire sub portions 32 have been extended back across the tube 18 over the same portion of the tube 18 where the respective exit point 29 is located and through a space normal to the respective exit points 29 to respective clamping locations 42 in the embedded space. The second non-embedded wire sub portions 32 have been clamped at the respective clamping locations 42 in clamps 43 configured to allow slippage of the wires 32 such that when the first and second non-embedded wire sub portions 31, 32 are rotated, a length of the second non-embedded wire sub portion 32 can slide out of the clamp 43 due to the pull on the wire 32 generated from the rotation and twisting of the first and second non-embedded wire sub portions 31, 32. In other words, the second non-embedded wire sub portions 32 could be said to be clamped loosely. This can be achieved by a low clamping force and/or a low friction or a combination thereof. After clamping of the second non-embedded wire sub portions 32, the respective first and second non-embedded wire sub portions 31, 32 are then rotated at the rotation location by rotating the hooks 51 driven by the electric motors 44 whereby the wires 31, 32 twist around each other until the wire breaks. That is to say, the steps S3 to S8 are repeated for both non-embedded wire portions respectively. FIG. 8 schematically shows what the twisting of the first and second non-embedded wire sub portions 31, 32 around each other looks like after a few rotations. In the embodiments shown there is a distance R, C of 0.5 or more but equal to or less than 10 working channel tube outer diameters D between the exit plane 36 and the rotation location 40, and between the exit plane 36 and the clamping location 42 respectively, the distance being measured perpendicularly to the exit plane 36. This is best seen in FIG. 7, where the distance R between the exit plane 36 and the portion of the clamp 52 that is closest to the exit plane 36 is more than 0.5 but less than one working channel tube outer diameter D, and the distance C between the exit plane 36 and the portion of the clamp 43 that is closest to the exit plane is close to one working channel tube outer diameter D.

As can be seen in FIG. 5, the non-embedded wire portion, towards the proximal end of the working channel tube 18, of which only the second non-embedded portion 32 is visible, extends substantially tangentially to the outer surface of the working channel tube 18. As can also be seen this is not the case for the first non-embedded wire sub portion 31 towards the distal end of the working channel tube 18 in detail BB. FIG. 6 is an enlarged view of detail BB in FIG. 5 where some of the press fit retainers 81 have been hidden for the purpose of illustration clarity. Here it can be seen that the rotation location 40 is located at an angle Ar to the exit point tangent line 34, and similarly that the clamping location 42 is located at a clamping angle Ac to the exit point tangent line 34. Both the rotation angle Ar and the clamping angle Ac are less than 25 degrees. Furthermore, the bend 41, the exit point 29 and the clamping location 42 can be seen.

Figure 7:
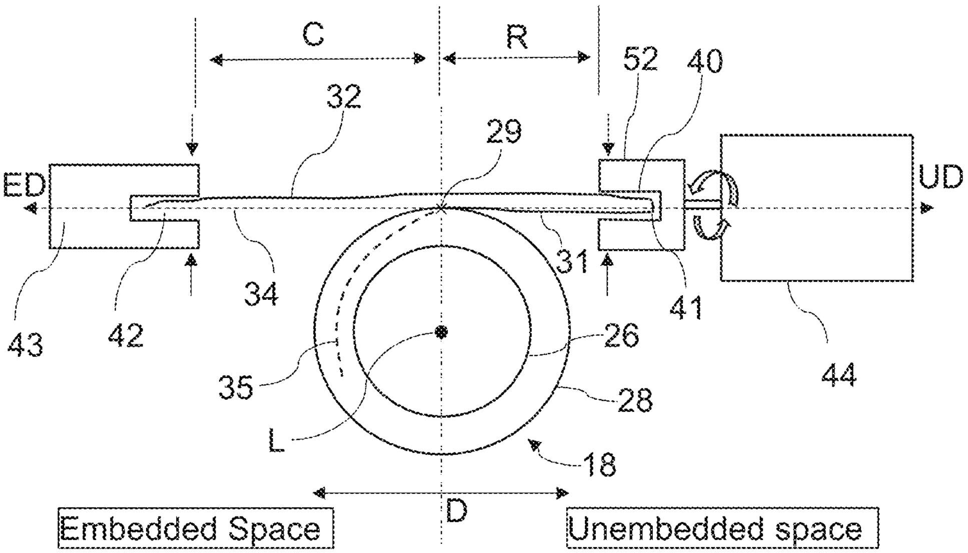
FIG. 7 shows a schematic illustration of a working channel tube during production according to another variation of the method of the present disclosure viewed in parallel with the longitudinal axis of the tube.
Figure 8:
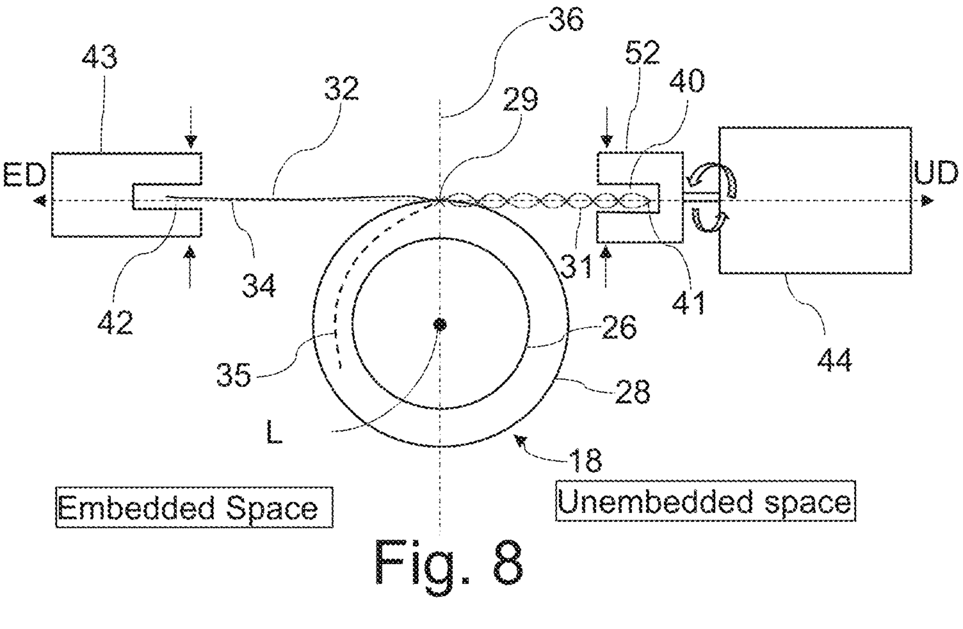
FIG. 8 shows the same view of the schematic illustration of FIG. 7 in a state where the non-embedded wire sub portions have been rotated a certain amount.
Figure 9:
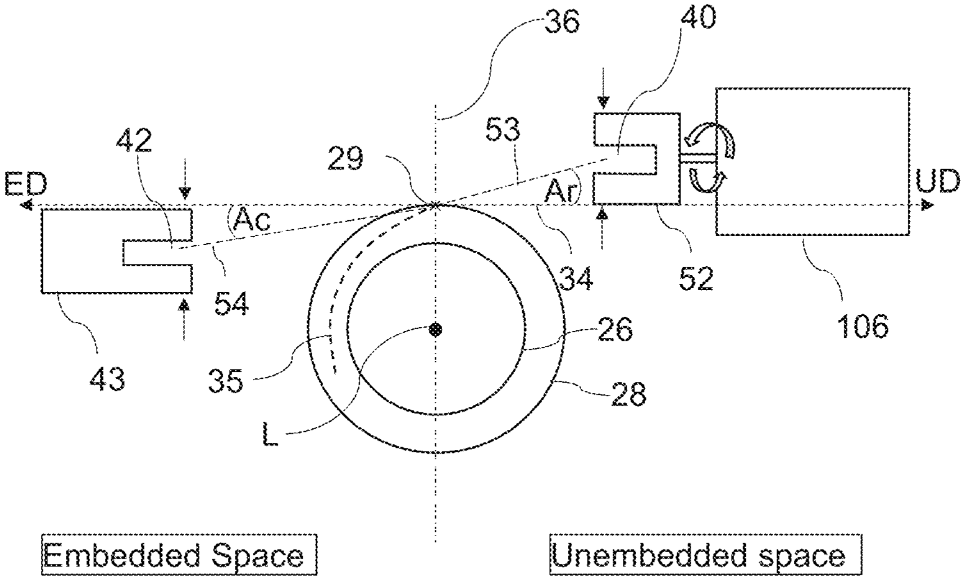
FIG. 9 shows another variation of the method according to the present disclosure, from the same vantage point as in FIG. 7 and FIG. 8.
Figure 10:
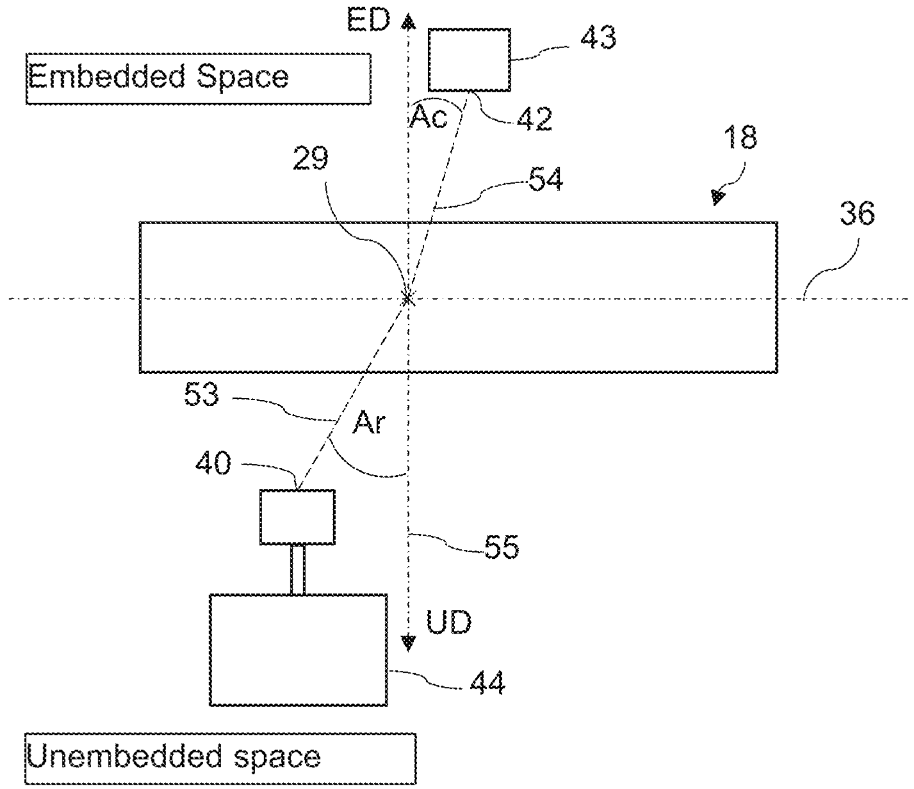
FIG. 10 shows a top-down view of a schematic illustration of a working channel tube during production according to another variation of the method according to the present disclosure.

In FIG. 7 and FIG. 8, the rotation location 40 and the clamping location 42 are located substantially on the exit point tangent line 34. This, however, need not be case as will be explained with reference to FIG. 9 and FIG. 10. As illustrated in FIG. 9, the rotation location 40 may be located such that a rotation angle Ar in a direction normal to the tube outer surface 28 at the exit point 29 between the exit point tangent line 34 and a straight line 53 extending from the exit point 29 to the rotation location 40 is 45 degrees or less, in this case about 30 degrees or less. The rotation angle Ar in general is preferably 45 degrees or less. The same is true for the clamping angle Ac between the exit point tangent line 34 and the straight line 54 extending between the exit point 29 and the clamping location 42, which in FIG. 9 (where the non-embedded wire has been hidden illustration clarity purposes) is approximately 30 degrees or less but in the opposite direction from the exit point tangent line 34 compared to the rotation angle Ar. In other embodiments, the rotation angle Ar may however also extend in the direction of the clamping angle Ac in FIG. 9, in fact both the rotation angle Ar and the clamping angle Ac may extend in any direction from the exit point tangent line 34 such as in a lateral direction away from a lateral plane 55 extending through the exit point 29 perpendicularly to the exit plane 36 as shown in FIG. 10. Preferably the rotation and clamping angles Ar, Ac are equal to or less than 45 degrees such as shown in the figures.

Figure 11:
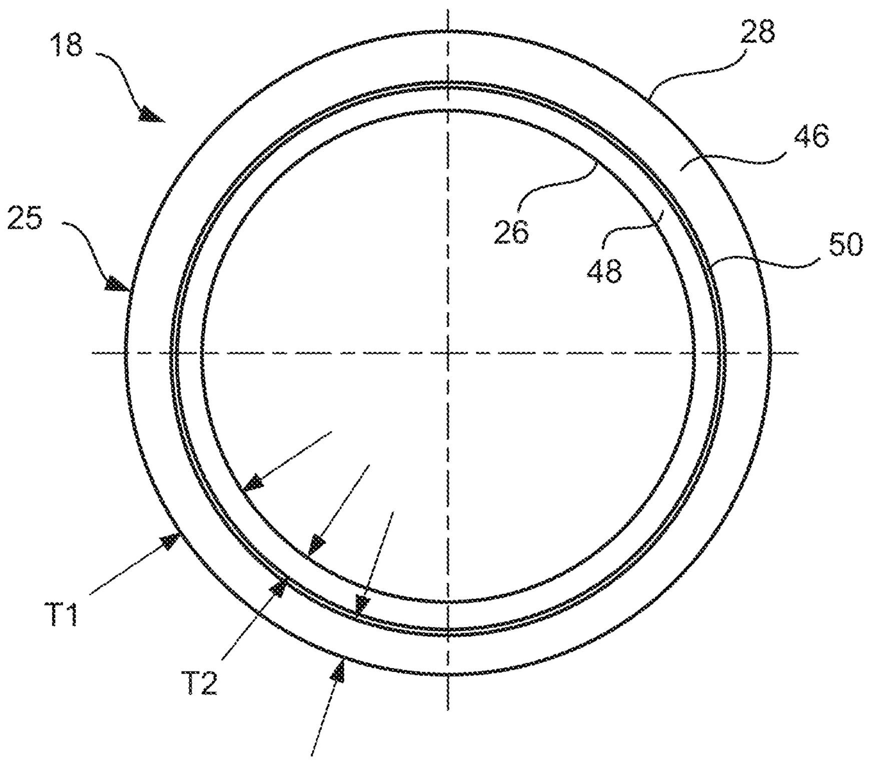
FIG. 11 shows a cross-section through a working channel tube according to an embodiment of the present disclosure.

FIG. 11 shows a cross-section through the working channel tube 18 according to an embodiment of the present disclosure. The working channel tube 18 has a circular cross-section and comprises two layers, namely an outer layer 46 and an inner layer 48. Both the outer layer 46 and the inner layer 48 are essentially hollow elongated tube bodies and are preferably made of different materials. The outer layer 46 is provided directly around the inner layer 48 or, said differently, the inner layer 48 is inserted into the outer layer 46. A primer 50 may be provided between the outer layer 46 and the inner layer 48 in order to ensure adherence between the outer layer 46 and the inner layer 48. E.g. the outer layer 46 may be made of thermoplastic polyurethane (TPU) and the inner layer 48 may be made of high-density polyethylene (HDPE). The layers may be coextruded. T1 represents the wall thickness. T2 represents the inner layer thickness. T3 represents the outer layer thickness. The outer surface 28 is smooth with no protrusions or the like.

The embodiment shown in FIG. 11 is only an example and it is evident that it may be also advantageous if the working channel tube 18 is not made of two parts (the outer layer 46 and the inner layer 48) but is made of one integral elongated working channel tube part having the outer surface 28 and the inner surface 26 and being made of a meltable plastic material.

Figure 12:
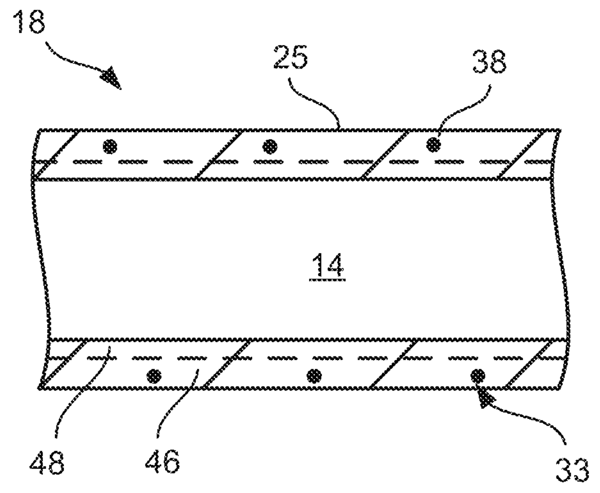
FIG. 12 shows a longitudinal sectional view of a working channel tube according to the present disclosure.

An embodiment according to which the working channel tube 18 is made of one integral part is shown in FIG. 12. FIG. 12 shows a longitudinal sectional view of a working channel tube 18 having a coil 33 embedded in a working channel tube 18. The wire 38 forming the coil 33 is covered by a material of the working channel tube 18 and is thus not exposed to (visible from) the outside.

According to another embodiment, the working channel tube 18 may have an outer diameter of 5.4±0.076 mm, an inner diameter of 4.4±0.076 mm and a tube wall thickness of 0.5 mm. The total length of the working channel tube 18 may be 1,500. The working channel tube 18 may comprise an outer layer 46, an inner layer 48 and a primer 50, which can also be designated as tie layer, between the outer layer 46 and the inner layer 48 as shown in FIG. 11. The material of the outer layer 46 may be a thermoplastic polyurethane like Pellethane® 2363-90AE with additives according to the especially preferred embodiment. E.g., the outer layer 46 may comprise 70% Pellethane® 2363-90AE and 30% additives. Among additives, it may be preferred if the outer layer 46 comprises an antimicrobial additive like BaSo4 and a friction reducing additive like ProPell™. The material of the inner layer 48 may be a high-density polyethylene like Borealis Bormed™ HE9621-PH. The material of the primer 50 or tie layer may be a linear low-density polyethylene-based tie resin like Orevac™ 18300M.

In this present embodiment, the wire coil wire has an outer diameter of 0.15 mm and is made from stainless steel SUS304 comprising a Br—Ni—Co coating.

The pitch of the coil 33 formed through the winding of the wire coil wire is 1 mm and the length of the section of the working channel tube 18, which is reinforced by the coil 33, is 115±5 mm. The section reinforced by the coil 32 has an inner diameter, which is greater than 4.2 mm, and an outer diameter, which is smaller than 5.4 mm.

The disclosure has been described with reference to exemplary embodiments. However, the scope of the invention is not limited to the illustrated embodiments, and alterations and modifications can be carried out without deviating from the scope of the invention.

Throughout the description, the use of the terms "first", "second", etc. does not imply any particular order or importance but are included to identify individual elements. Furthermore, the labelling of a first element does not imply the presence of a second element and vice versa.

The following items are further variations and examples of the embodiments described with reference to the figures.

1. A method for producing a wire coil reinforced working channel tube for an endoscope, the method comprising: A) providing a working channel tube reinforced with a wire coil that is embedded between an inner and outer surface of the working channel tube, wherein a non-embedded wire portion of the wire coil extends out of the outer surface of the tube from an exit point, wherein an exit point tangent line that is tangent to the outer surface at the exit point defines two opposite directions extending away from the exit point: an unembedded direction extending away from a final embedded wire portion leading up to the exit point, and an embedded direction that is opposite the unembedded direction, wherein an exit plane extends through the exit point and a longitudinal axis of the tube, the space extending in the unembedded and embedded directions from the exit plane being defined as the unembedded space and embedded space, respectively; B) fixating the working channel tube; C) extending the non-embedded wire portion from the exit point to a rotation location located in the unembedded space; D) bending the non-embedded wire portion at the rotation location forming a bend and a first non-embedded wire sub portion extending from the exit point to the bend and a second non-embedded wire sub portion extending after the bend; E) extending the second non-embedded wire sub portion back across the tube to a clamping location located in the embedded space; F) clamping the second non-embedded wire sub portion at the clamping location in a clamp; and G) rotating the non-embedded wire sub portions at the rotation location such that the first and second non-embedded wire sub portions twist around each other until the wire breaks.
2. Method according to item 1, wherein the clamp in which the second non-embedded wire sub portion is clamped in is configured to allow slippage of the wire such that a length of the wire slides out of the clamp when pulled.
3. Method according to any one of the preceding items, wherein the rotation location is located in the unembedded space such that a rotation angle in a direction normal to the exit point and the tube outer surface between a straight line extending from the exit point to the rotation location and the exit point tangent line is 45 degrees or less.
4. Method according to any one of the preceding items, wherein the clamping location is located in the embedded space such that a clamping angle between the exit point tangent line and a straight line extending from the exit point to the clamping location is 45 degrees or less.
5. Method according to any one of the preceding items, wherein the rotation angle and the clamping angle is equal to or less than 10 degrees.
6. Method according to any one of the preceding items, wherein there is a distance of 0.5 or more, but equal to or less than 10 working channel tube outer diameters between the exit plane and the rotation location and between the exit plane and the clamping location respectively, the distance being measured perpendicularly to the exit plane.
7. Method according to any one of the preceding items, wherein a second non-embedded wire portion of the wire coil extends out of the outer surface of the tube from a different second exit point defining respective unembedded and embedded directions, wherein steps C) to G) are performed for the second non-embedded wire portion respectively.

8. Method according to any one of the preceding items, wherein the working channel tube is fixated such that there is a fixation location within 10 working channel tube outer diameters or less proximally of each respective exit point and a fixation location within 10 working channel tube outer diameters or less distally of each respective exit point.
9. Method according to any one of the preceding items, wherein a rod is inserted into the working channel tube before fixating the working channel tube in place.
10. Method according to item 9, wherein the rod is at least inserted a length such that it extends inside the working channel tube at each location the working channel tube is fixated and/or at each exit point.
11. Method according to any one of the preceding items wherein the embedded wire coil extends equal to or less than three quarters of a length of the working channel tube.
12. Method according to any one of the preceding items, wherein at least an outer layer of the working channel tube is made from a plastic material.
13. A reinforced working channel tube produced according to the method of any one of items 1-12.
14. An endoscope comprising a reinforced working channel tube according to item 13.
15. A visualization system comprising a video processing apparatus and an endoscope according to or 14, wherein the video processing apparatus (VPA) is couplable to the endoscope and capable of processing an image recorded by the endoscope and outputting the image on a display.

LIST OF REFERENCE SIGNS

2 endoscope
4 endoscope handle
6 insertion cord
8 insertion tube
10 bending section
12 distal tip unit
14 working channel
16 working channel access port
18 working channel tube
20 first operating unit
22 second operating unit
25 working channel tube wall
26 inner surface
28 outer surface
29 exit point
30 non-embedded wire portion
31 first non-embedded wire sub portion
32 second non-embedded wire sub portion
33 wire coil
34 exit point tangent line
35 final embedded wire portion
36 exit plane
38 wire coil wire
40 rotation location
41 bend
42 clamping location
43 clamp
44 rotator
46 outer layer
48 inner layer
50 primer
51 hook
52 clamp
53 Straight line between exit point and rotation location
54 Straight line between exit point and clamping location
55 Lateral plane
60 segment
62 hinge
64 steering cable
66 steering cable guide
68 wires
70 spacing
72 cut-out lobe
80 rod
81 press fit retainer
100 visualization system
102 video processing apparatus
104 display screen
106 cable connector
T1 wall thickness
T2 inner layer thickness
T3 outer layer thickness
L longitudinal axis
Ar rotation angle
Ac clamping angle
UD unembedded direction
ED embedded direction
D working channel tube outer diameter
R distance between exit plane and rotation location
C distance between exit plane and clamping location

The invention claimed is:

1. A method of making a working channel tube for an endoscope, the method comprising:
providing a tube reinforced with a wire embedded between an inner surface and an outer surface of the tube, a non-embedded wire portion of the wire extending, at an exit point, from the outer surface, an embedded wire portion of the wire extending, from the exit point, between the inner surface and the outer surface;
fixating the working channel tube in a releasable manner to a support structure;
bending the non-embedded wire portion at a distance from the exit point to form a bend, a first non-embedded wire sub portion extending from the exit point to the bend, and a second non-embedded wire sub portion extending from the bend;
extending the second non-embedded wire sub portion from the bend across the working channel tube; and
twisting together the first non-embedded wire sub portion and the second non-embedded wire sub portion until the wire breaks,
wherein the wire breaks at the exit point or beneath the outer surface without protruding from the outer surface.

2. The method of claim 1, the method further comprising, prior to said twisting, securing the second non-embedded wire sub portion at a securing point, the second non-embedded wire sub portion thus extending from the bend across the tube to the securing point at an angle less than 45 degrees to a line normal to a longitudinal axis of the tube.

3. The method of claim 1, the method further comprising, while twisting, tensioning the second non-embedded wire sub portion less than the first non-embedded wire sub portion.

4. The method of claim 1, wherein the method further comprises:
prior to said twisting, engaging the second non-embedded wire sub portion at a rotation location, the second non-embedded wire sub portion thus extending from the bend across the working channel tube to the rotation location at an angle less than 45 degrees to a line normal to a longitudinal axis of the working channel tube, said engaging allowing the second non-embedded wire sub portion to slip through the rotation location;

said twisting causing tensioning the first non-embedded wire sub portion and the second non-embedded wire sub portion; and said engaging of the second non-embedded wire sub portion allowing the second non-embedded wire sub portion to slip on the rotation location and thus maintain a tension in the second non-embedded wire sub portion lower than a tension in the first non-embedded wire sub portion.

5. The method of claim 4, wherein said method further comprises providing a wire twisting machine including the support structure, a hook including the rotation location, and a clamp, the hook and the clamp positioned on opposite sides of the longitudinal axis of the working channel tube, the second non-embedded wire sub portion thus extending from the bend across the working channel tube to the hook, wherein the clamp slidingly retains the tension in the second non-embedded wire sub portion, the method further comprising causing the wire twisting machine to rotate the clamp to twist the first non-embedded wire sub portion and the second non-embedded wire sub portion until the wire breaks.

6. A method of making a working channel tube for an endoscope, the method comprising:

a) providing a tube reinforced with a wire that is coiled and embedded between an inner surface and an outer surface of the tube, wherein a non-embedded wire portion of the wire extends out of the outer surface of the working channel tube from an exit point, wherein an exit point tangent line that is tangent to the outer surface at the exit point defines two opposite directions extending away from the exit point:

i. an unembedded direction extending away from a final embedded wire portion leading up to the exit point; and ii. an embedded direction that is opposite the unembedded direction;

wherein an exit plane extends through the exit point and a longitudinal axis of the working channel tube, the space extending in the unembedded and embedded directions from the exit plane being defined as the unembedded space and embedded space, respectively;

b) fixating the tube;

c) extending the non-embedded wire portion from the exit point to a rotation location located in the unembedded space;

d) bending the non-embedded wire portion at the rotation location forming a bend, a first non-embedded wire sub portion extending from the exit point to the bend, and a second non-embedded wire sub portion extending after the bend;

e) extending the second non-embedded wire sub portion across the tube to a clamping location located in the embedded space;

f) clamping the second non-embedded wire sub portion at the clamping location in a clamp; and g) rotating the first non-embedded wire sub portion and the second non-embedded wire sub portion at the rotation location to twist the first and second non-embedded wire sub portions around each other until the wire breaks.

7. The method of claim 6, wherein the clamp is configured to allow slippage of the wire when the wire is pulled, wherein the rotation location is located in the unembedded space such that a rotation angle in a direction normal to the exit point and the tube outer surface between a straight line extending from the exit point to the rotation location and the exit point tangent line is 45 degrees or less, and wherein the clamping location is located in the embedded space such that a clamping angle between the exit point tangent line and a straight line extending from the exit point to the clamping location is 45 degrees or less.

8. The method of claim 6, wherein the clamp is configured to allow slippage of the wire when the wire is pulled.

9. The method of claim 6, wherein the rotation location is located in the unembedded space such that a rotation angle in a direction normal to the exit point and the tube outer surface between a straight line extending from the exit point to the rotation location and the exit point tangent line is 45 degrees or less.

10. The method of claim 6, wherein the clamping location is located in the embedded space such that a clamping angle between the exit point tangent line and a straight line extending from the exit point to the clamping location is 45 degrees or less.

11. The method of claim 6, wherein there is a distance of 0.5 or more, but equal to or less than 10, tube outer diameters between the exit plane and the rotation location and between the exit plane and the clamping location, respectively, the distance being measured perpendicularly to the exit plane.

12. The method of claim 11, wherein the tube is fixated such that there is a fixation location within 10 or fewer tube outer diameters on both sides, longitudinally, of the exit point.

13. The method of claim 12, wherein a rod is inserted into the tube before fixating the tube in place, and wherein the rod is at least inserted a length such that it extends inside the tube to each fixation location.

14. The method of claim 6, wherein a rod is inserted into the tube before fixating the tube in place.

15. The method of claim 14, wherein the rod is at least inserted a length such that it extends inside the tube at each location the tube is fixated and/or at each exit point.

16. The method of claim 6, wherein a second non-embedded wire portion of the wire extends out of the outer surface of the tube from a different second exit point defining respective unembedded and embedded directions, wherein steps c) to g) are performed for the second non-embedded wire portion respectively.

17. The method of claim 16, wherein the wire is embedded and coiled between the exit point and the second exit point, a longitudinal distance between the exit point and the second exit point being equal to or less than three quarters of a length of the tube.

18. The method of claim 6, wherein at least an outer layer of the tube is made from a plastic material.

19. The method of claim 6, wherein the wire breaks at the exit point or beneath the outer surface such that the wire does not protrude from the outer surface.

* * * * *